United States Patent
Lee et al.

(10) Patent No.: US 6,172,110 B1
(45) Date of Patent: Jan. 9, 2001

(54) ACYLATED BETULIN AND DIHYDROBETULIN DERIVATIVES, PREPARATION THEREOF AND USE THEREOF

(75) Inventors: Kuo-Hsiung Lee; I-Chen Sun, both of Chapel Hill; Hui-Kang Wang, Carrboro, all of NC (US); Louis Mark Cosentino, Springfield, VA (US)

(73) Assignees: The University of North Carolina at Chapel Hill, Chapel Hill, NC (US); BBI Biotech Research Laboratories, Inc., Gaithersburg, MD (US)

(*) Notice: Under 35 U.S.C. 154(b), the term of this patent shall be extended for 0 days.

(21) Appl. No.: 09/260,078

(22) Filed: Mar. 2, 1999

Related U.S. Application Data

(60) Provisional application No. 60/076,449, filed on Mar. 2, 1998.

(51) Int. Cl.[7] .................. A61K 31/225; C07C 69/013
(52) U.S. Cl. .................. 514/530; 514/548; 560/182; 560/194
(58) Field of Search .................. 560/182, 194; 514/530, 548

(56) References Cited

U.S. PATENT DOCUMENTS 5,468,888 * 11/1995 Bouboutou et al. .
5,679,828 * 10/1997 Lee et al. .

FOREIGN PATENT DOCUMENTS

01143832 * 6/1989 (JP) .

OTHER PUBLICATIONS

Pasich, J. "Emulsifiers from terpenoid compounds. Part VIII. Physical–chemical study of betulin and its esters." *Herba Pol.* vol. 25 No. 2 pp. 147–153. See abstract, 1979.*

Dalgleish, A.G. et al., "The CD4 (T4) antigen is an essential component of the receptor for the AIDS retrovirus," *Nature* 312:763–767 (1984).

Evers, M. et al., "Betulinic Acid Derivatives: A New Class of Human Immunodeficiency Virus Type I Specific Inhibitors with a New Mode of Action," *J. Med. Chem.* 39:1056–1068 (1996).

Fujioka, T. et al., "Anti–AIDS Agents, 11. Betulinic Acid and Platanic Acid as Anti–HIV Principles from *Syzigium claviflorum*, and the Anti–HIV Activity of Structurally Related Triterpenoids," *J. Nat. Prod.* 57:243–247 (1994).

Hashimoto, F. et al., "Anti–AIDS Agents–XXVII. Synthesis and Anti–HIV Activity of Betulinic Acid and Dihydrobetulinic Acid Derivatives," *Bioorg. Med. Chem.* 5:2133–2143 (1997).

Kashiwada, Y. et al., "Betulinic Acid Dihydrobetulinic Acid Derivatives as Potent Anti–HIV Agents," *J.Med. Chem.* 39:1016–1017 (1996).

English Language abstract of JP 1–143832 (Document AL1), Derwent World Patents, Index, WPI Accession No. 89–204083/198928.

Vasnev, V.V. et al., "Synthesis of unsaturated polyesters containing betulinol moieties," *Makromol. Chem.* 188:683–691 (1987).

International Search Report for International Application No. PCT/US99/04605, mailed Jun. 3, 1999.

* cited by examiner

*Primary Examiner*—Gary Geist
*Assistant Examiner*—Leigh C. Maier
(74) *Attorney, Agent, or Firm*—Sterne, Kessler, Goldstein & Fox P.L.L.C.

(57) ABSTRACT

Betulin and dihydrobetulin acyl derivatives according to the present invention have been found to have potent anti-HIV activity. The compounds of the present invention have the following formulae:

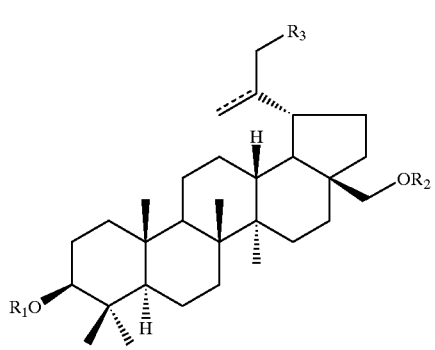

or pharmaceutically acceptable salts thereof, wherein $R_1$ is a $C_2$–$C_{20}$ substituted or unsubstituted carboxyacyl, $R_2$ is a $C_2$–$C_{20}$ substituted or unsubstituted carboxyacyl; and $R_3$ is hydrogen, halogen, amino, optionally substituted mono- or di-alkylamino, or —$OR_4$, where $R_4$ is hydrogen, $C_{1-4}$ alkanoyl, benzoyl, or $C_2$–$C_{20}$ substituted or unsubstituted carboxyacyl; wherein the dashed line represents an optional double bond between C20 and C29.

33 Claims, No Drawings

ACYLATED BETULIN AND DIHYDROBETULIN DERIVATIVES, PREPARATION THEREOF AND USE THEREOF

CROSS-REFERENCE TO RELATED APPLICATIONS

This application claims the benefit of U.S. Provisional Application No. 60/076,449, filed Mar. 2, 1998, and entirely incorporated by reference herein.

STATEMENT AS TO RIGHTS TO INVENTIONS MADE UNDER FEDERALLY-SPONSORED RESEARCH AND DEVELOPMENT

Part of the work performed during development of this invention utilized U.S. Government funds under grant AI-33066 from the National Institute of Allergies and Infectious Diseases. The U.S. Government has certain rights in this invention.

BACKGROUND OF THE INVENTION

1. Field of the Invention

The present invention relates to novel synthetic derivatives of betulin and dihydrobetulin, and the use of such derivatives as pharmaceuticals.

2. Related Art

Retroviruses are small, single-stranded positive-sense RNA viruses. A retroviral particle comprises two identical single-stranded positive sense RNA molecules. Their genome contains, among other things, the sequence of the RNA-dependent DNA polymerase, also known as reverse transcriptase. Many molecules of reverse transcriptase are found in close association with the genomic RNA in the mature viral particles. Upon entering a cell, this reverse transcriptase produces a double-stranded DNA copy of the viral genome, which is then inserted into the chromatin of a host cell. Once inserted, the viral sequence is called a provirus. Retroviral integration is directly dependent upon viral proteins. Linear viral DNA termini (the LTRs) are the immediate precursors to the integrated proviral DNA. There is a characteristic duplication of short stretches of the host's DNA at the site of integration.

Progeny viral genomes and mRNAs are transcribed from the inserted proviral sequence by host cell RNA polymerase in response to transcriptional, regulatory signals in the terminal regions of the proviral sequence, the long terminal repeats, or LTRs. The host cell's protein production machinery is used to produce viral proteins, many of which are inactive until processed by virally encoded proteases. Typically, progeny viral particles bud from the cell surface in a non-lytic manner. Retroviral infection does not necessarily interfere with the normal life cycle of an infected cell or organism. However, neither is it always benign with respect to the host organism. While most classes of DNA viruses can be implicated in tumorigenesis, retroviruses are the only taxonomic group of RNA viruses that are oncogenic. Various retroviruses, such as the Human Immunodeficiency Virus (HIV), which is the etiological agent responsible for acquired immune deficiency syndrome (AIDS) in humans, are also responsible for several very unusual diseases of the immune system of higher animals.

Human Immunodeficiency Virus (HIV) is a member of the lentiviruses, a subfamily of retroviruses. Many retroviruses are well-known carcinogens. HIV per se is not known to cause cancer in humans or other animals, but it does present a formidable challenge to the host. The viral genome contains many regulatory elements which allow the virus to control its rate of replication in both resting and dividing cells. Most importantly, HIV infects and invades cells of the immune system; it breaks down the body's immune system and renders the patient susceptible to opportunistic infections and neoplasms. The immune defect appears to be progressive and irreversible, with a high mortality rate that approaches 100% over several years.

HIV-1 is trophic and cytopathic for T4 lymphocytes, cells of the immune system which express the cell surface differentiation antigen CD4, also known as OKT4, T4 and leu3. The viral tropism is due to the interactions between the viral envelope glycoprotein, gp120, and the cell-surface CD4 molecules (Dalgleish et al., Nature 312:763–767 (1984)). These interactions not only mediate the infection of susceptible cells by HIV, but are also responsible for the virus-induced fusion of infected and uninfected T cells. This cell fusion results in the formation of giant multinucleated syncytia, cell death, and progressive depletion of CD4 cells in HIV-infected patients. These events result in HIV-induced immunosuppression and its subsequent sequelae, opportunistic infections and neoplasms.

In addition to CD4+ T cells, the host range of HIV includes cells of the mononuclear phagocytic lineage (Dalgleish et al, supra), including blood monocytes, tissue macrophages, Langerhans cells of the skin and dendritic reticulum cells within lymph nodes. HIV is also neurotropic, capable of infecting monocytes and macrophages in the central nervous system causing severe neurologic damage. Macrophage/monocytes are a major reservoir of HIV. They can interact and fuse with CD4-bearing T cells, causing T cell depletion and thus contributing to the pathogenesis of AIDS.

Considerable progress has been made in the development of drugs for HIV-1 therapy during the past few years. There are now 12 drugs approved for use in the U.S., including five nucleoside analog reverse transcriptase inhibitors (AZT, 3TC, ddI, ddC, and D4T), three non-nucleoside RT inhibitors (nevirapine, delavirdine, and efavirenz) and four protease inhibitors (saquinavir, ritonavir, indinavir, and nelfinavir). Combinations of these drugs are particularly effective and can reduce levels of viral RNA to undetectable levels in the plasma and slow the development of viral resistance, with resulting improvements in patient health and life span.

Despite these advances, there are still problems with the currently available drug regimens. Many of the drugs exhibit severe toxicities, have other side-effects (e.g., fat redistribution) or require complicated dosing schedules that reduce compliance and thereby limit efficacy. Resistant strains of HIV often appear over extended periods of time even on combination therapy. The high cost of these drugs is also a limitation to their widespread use, especially outside of developed countries.

There is still a major need for the development of additional drugs to circumvent these issues. Ideally these would target different stages in the viral life cycle, adding to the armamentarium for combination therapy, and exhibit minimal toxicity, yet have lower manufacturing costs.

Previously, betulinic acid and platanic acid were isolated as anti-HIV principles from Syzigium claviflorum. Betulinic acid and platanic acid exhibited inhibitory activity against HIV-1 replication in H9 lymphocyte cells with $EC_{50}$ values of 1.4 μM and 6.5 μM, respectively, and T.I. values of 9.3 and 14, respectively. Hydrogenation of betulinic acid yielded dihydrobetulinic acid, which showed slightly more potent anti-HIV activity with an $EC_{50}$ value of 0.9 and a T.I. value of 14 (Fujioka, T., et al., *J Nat. Prod.* 57:243–247 (1994)).

Esterification of betulinic acid (1) with certain substituted acyl groups, such as 3',3'-dimethylglutaryl and 3',3'-dimethylsuccinyl groups produced derivatives having enhanced activity (Kashiwada, Y., et al., *J. Med Chem.* 39:1016–1017 (1996)). Acylated betulinic acid and dihydrobetulinic acid derivatives that are potent anti-HIV agents are also described in U.S. Pat. No. 5,679,828.

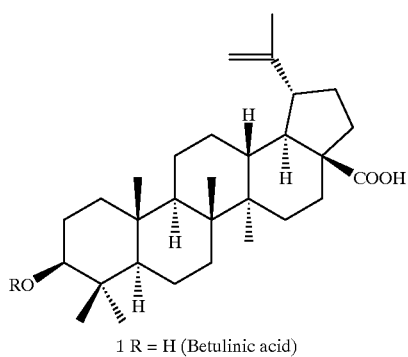

1 R = H (Betulinic acid)

U.S. Pat. No. 5,468,888 discloses 28-amido derivatives of lupanes that are described as having a cytoprotecting effect for HIV-infected cells.

Japanese Patent Application No. J 01 143,832 discloses that betulin (3) and 3,28-diesters thereof are useful in the anti-cancer field.

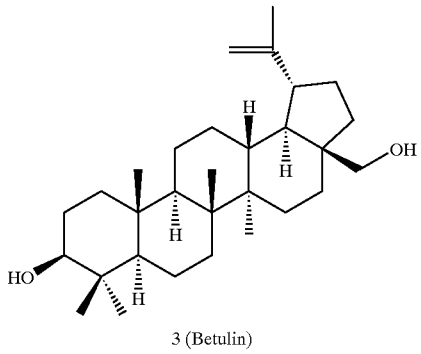

3 (Betulin)

A need continues to exist for compounds which possess potent anti-HIV activity with different modes of action. Such compounds are urgently needed to add to existing anti-HIV therapies.

SUMMARY OF THE INVENTION

A first aspect of the present invention is directed to novel compounds of Formula I:

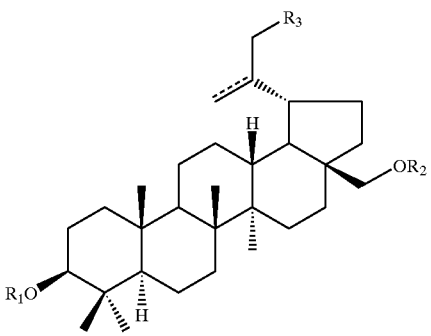

I or pharmaceutically acceptable salts thereof; wherein $R_1$ is a $C_2$–$C_{20}$ substituted or unsubstituted carboxyacyl, $R_2$ is a $C_2$–$C_{20}$ substituted or unsubstituted carboxyacyl; and $R_3$ is hydrogen, halogen, amino, optionally substituted mono- or di-alkylamino, or —$OR_4$, where $R_4$ is hydrogen, $C_{1-4}$ alkanoyl, benzoyl, or $C_2$–$C_{20}$ substituted or unsubstituted carboxyacyl;

wherein the dashed line represents an optional double bond between C20 and C29.

A second aspect of the present invention is directed to pharmaceutical compositions, comprising one or more compounds of Formula I, and a pharmaceutically acceptable carrier or diluent. One or more additional pharmaceutically active compounds can also be included in these compositions.

The compounds are useful as anti-retroviral agents. Therefore, a third aspect of the present invention is directed to methods for inhibiting a retroviral infection in cells or tissue of an animal, comprising administering an effective retroviral inhibiting amount of a compound of Formula I. A preferred embodiment is directed to a method for treating a patient suffering from a retroviral-related pathology, comprising administering to said subject a retroviral inhibiting effective amount of a pharmaceutical composition that includes a compound of Formula I.

A fourth aspect of the present invention is directed to a method for making compounds of Formula I.

DETAILED DESCRIPTION OF THE PREFERRED EMBODIMENTS

The compounds of the present invention have the general Formula I:

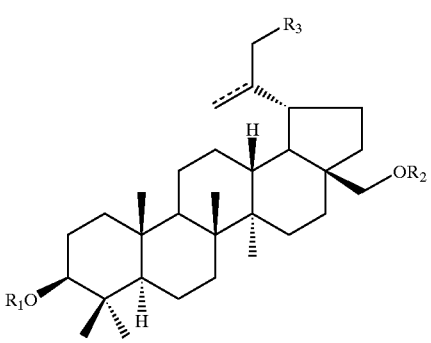

I or a pharmaceutically acceptable salt thereof: wherein $R_1$ is a $C_2$–$C_{20}$ substituted or unsubstituted carboxyacyl, $R_2$ is a $C_2$–$C_{20}$ substituted or unsubstituted carboxyacyl; and $R_3$ is hydrogen, halogen, amino, optionally substituted mono- or di-alkylamino, or —$OR_4$, where $R_4$ is hydrogen, $C_{1-4}$ alkanoyl, benzoyl, or $C_2$–$C_{20}$ substituted or unsubstituted carboxyacyl;

wherein the dashed line represents an optional double bond between C20 and C29.

Preferred compounds of the present invention are those where:

$R_1$ and $R_2$ are each $C_2$–$C_{20}$ substituted or unsubstituted carboxyacyl, and $R_3$ is hydrogen. In one embodiment, the bond between C20 and C29 is a double bond. In another embodiment, the bond between C20 and C29 is a single bond.

Another group of preferred compounds are those where:

$R_1$ and $R_2$ are each $C_2$–$C_{20}$ substituted or unsubstituted carboxyacyl, and $R_3$ is halogen or —$OR_4$, where $R_4$ is $C_2$–$C_{20}$ substituted or unsubstituted carboxyacyl. In one embodiment, the bond between C20 and C29 is a double bond. In another embodiment, the bond between C20 and C29 is a single bond.

Even more preferred are those compounds wherein $R_1$ and $R_2$ are each a $C_4$–$C_{16}$ carboxyalkanoyl group that is mono- or di- substituted at the 3' carbon atom. Such a side chain has the formula:

—C(O)CH₂CR'R''(CH₂)$_b$COOH where

R' and R'' are each $C_{1-4}$ alkyl, preferably methyl or ethyl, or R' is hydrogen and R'' is $C_{1-4}$ alkyl, or R' and R'' are taken together to form a di-, tri, tetra- or pentamethylene linkage, and b is from zero to twelve, preferably zero to 4, most preferably zero or 1.

Additionally preferred are those compounds where $R_1$ and $R_2$ are both a $C_4$–$C_{16}$ carboxyalkoxyacetyl group of the formula:

—C(O)CH₂O(CH₂)$_a$COOH, where a is from one to ten, preferably one to four, most preferably one or two.

Preferred values of $R_3$ include: hydrogen, halogen, or —$OR_4$, where $R_4$ is preferably hydrogen; —C(O)CH₂CR'R''(CH₂)$_b$COOH, where R', R'' and b are as defined above; or —C(O)CH₂O(CH₂)$_a$COOH, where a is as defined above.

Particularly preferred compounds are those of Formula I, wherein:

$R_1$ and $R_2$ are each one of:

[chemical structures]

$R_3$ is preferably hydrogen, chloro, bromo, or hydroxy or is one of:

[chemical structures]

Betulin and dihydrobetulin acyl derivatives according to the present invention have been found to have potent anti-HIV activity. The C3-hydroxy, C28-hydroxy and C20-exomethylene groups in betulin can be easily modified. It has been found that introducing a $C_2$ to $C_{20}$ substituted or unsubstituted acyl group at the C3-hydroxy or C28-hydroxy groups of betulin and dihydrobetulin readily produces the corresponding 3-O-acyl, 28-O-acyl, and/or 28-O-acyl derivatives.

The C3 and C28 acyl groups of the most active compounds have dimethyl groups or oxygen at the C3 position. This observation suggests that this type of acyl group might be important to the enhanced anti-HIV activity.

The invention is also directed to a method for treating a subject infected with HIV-1 by administering at least one of the above-noted betulin derivatives, optionally in combination with any one or more of the known anti-AIDS therapeutics or an immunostimulant.

Other features, advantages, embodiments, aspects and objects of the present invention will be clear to those skilled in the areas of relevant art, based upon the description, teaching and guidance presented herein.

The compounds of the present invention have been discovered to have anti-retroviral activity, thus providing suitable compounds and compositions for treating retroviral infections, optionally with additional pharmaceutically active ingredients, such as anti-retroviral, anti-HIV, and/or immuno-stimulating compounds or antiviral antibodies or fragments thereof.

By the term "anti-retroviral activity" or "anti-HIV activity" is intended the ability to inhibit at least one of:

(1) viral pro-DNA integration into host cell genome;
(2) retroviral attachment to cells;
(3) viral entry into cells;
(4) cellular metabolism which permits viral replication;
(5) inhibition of intercellular spread of the virus;
(6) synthesis and/or cellular expression of viral antigens;
(7) activity of virus-coded enzymes (such as reverse transcriptase, integrase and proteases); and/or
(8) any known retroviral or HIV pathogenic actions, such as, for example, immunosuppression. Thus, any activity which tends to inhibit any of these mechanisms is "anti-retroviral activity" or "anti-HIV activity."

A betulin or dihydrobetulin derivative of the present invention can be used for treatment of retroviral (e.g., HIV) infection either alone, or in combination with other modes of therapy known in the art. Such modes of therapy can include chemotherapy with drugs, such as, but not limited to, at least one of AZT, ddC, ddA, d4T, ddI, or any other antiretroviral drugs or antibodies in combination with each other, or associated with a biologically based therapeutic, such as, for example, soluble CD4, antibodies to CD4, and conjugates of CD4 or anti-CD4, or as additionally presented herein.

Because the betulin or dihydrobetulin derivatives of the present invention are relatively less or substantially non-toxic to normal cells, their utility is not limited to the treatment of established retroviral infections. For example, a betulin derivative according to the present invention can be used in treating blood products, such as those maintained in blood banks. The nation's blood supply is currently tested for antibodies to HIV. However, the test is still imperfect and samples which yield negative tests can still contain HIV virus. Treating the blood and blood products with the betulin derivatives of the present invention can add an extra margin of safety by killing any retrovirus that may have gone undetected.

Pharmaceutical Compositions

Pharmaceutical compositions of the present invention can comprise at least one of the betulin or dihydrobetulin derivatives. Pharmaceutical compositions according to the present invention can also further comprise other anti-viral agents such as, but not limited to, AZT (Glaxo Wellcome), 3TC (Glaxo Wellcome), ddI (Bristol-Myers Squibb), ddC (Hoffmann-La Roche), D4T (Bristol-Myers Squibb), abacavir (Glaxo Wellcome), nevirapine (Boehringher Ingelheim), delavirdine (Pharmacia and Upjohn), efavirenz (DuPont Pharmaceuticals), saquinavir (Hoffmann-La Roche), ritonavir (Abbott Laboratories), indinavir (Merck and Company), nelfinavir (Agouron Pharmaceuticals), amprenavir (Glaxo Wellcome), adefovir (Gilead Sciences) and hydroxyurea (Bristol-Meyers Squibb).

Additional suitable antiviral agents for optimal use with a betulin derivative of the present invention can include, but are not limited to, AL-721 (lipid mixture) manufactured by Ethigen Corporation and Matrix Research Laboratories; Amphotericin B methyl ester; Ampligen (mismatched RNA) developed by DuPont/HEM Research; anti-AIDS antibody (Nisshon Food); 1 AS-101 (heavy metal based immunostimulant); Betaseron (β-interferon) manufactured by Triton Biosciences (Shell Oil); butylated hydroxytoluene; Carrosyn (polymannoacetate); Castanospermine; Contracan (stearic acid derivative); Creme Pharmatex (containing benzalkonium chloride) manufactured by Pharmalec; CS-87 (5-unsubstituted derivative of Zidovudine), Cytovene (ganciclovir) manufactured by Syntex Corporation; dextran sulfate; D-penicillamine (3-mercapto-D-valine) manufactured by Carter-Wallace and Degussa Pharmaceutical; Foscarnet (trisodium phosphonoformate) manufactured by Astra AB; fusidic acid manufactured by Leo Lovens; glycyrrhizin (a constituent of licorice root); HPA-23 (ammonium-21-tungsto-9-antimonate) manufactured by Rhone-Poulenc Santé; human immune virus antiviral developed by Porton Products International; Ornidyl (eflornithine) manufactured by Merrell-Dow; nonoxinol; pentamidine isethionate (PENTAM-300) manufactured by Lypho Med; Peptide T (octapeptide sequence) manufactured by Peninsula Laboratories; Phenytoin (Warner-Lambert); Ribavirin; Rifabutin (ansamycin) manufactured by Adria Laboratories; CD4-IgG2 (Progenics Pharmaceuticals) or other CD4-containing or CD4-based molecules; T-20 (Trimeris); Trimetrexate manufactured by Warner-Lambert Company; SK-818 (germanium-derived antiviral) manufactured by Sanwa Kagaku; suramin and analogues thereof manufactured by Miles Pharmaceuticals; UA001 manufactured by Ueno Fine Chemicals Industry; and Wellferon (α-interferon) manufactured by Glaxo Wellcome.

Pharmaceutical compositions of the present invention can also further comprise immunomodulators. Suitable immunomodulators for optional use with a betulin derivative of the present invention in accordance with the present invention can include, but are not limited to: ABPP (Bropririmine); Ampligen (mismatched RNA) DuPont/HEM Research; anti-human interferon-α-antibody (Advance Biotherapy and Concepts); anti-AIDS antibody (Nisshon Food); AS-101 (heavy metal based immunostimulant; ascorbic acid and derivatives thereof; interferon-β; Carrosyn (polymannoacetate); Ciamexon (Boehringer-Mannheim); cyclosporin; cimetidine; CL-246,738 (American Cyanamid); colony stimulating factors, including GM-CSF (Sandoz, Genetics Institute); dinitrochlorobenzene; HE2000 (Hollis-Eden Pharmaceuticals); interferon-α; inteferon-gamma; glucan; hyperimmune gamma-globulin (Bayer); IMREG-1 (leukocyte dialyzate) and IMREG-2 (IMREG Corp.); immuthiol (sodium diethylthiocarbamate) (Institut Merieux); interleukin-1 (Cetus Corporation; Hoffmann-LaRoche; Immunex); interleukin-2 (IL-2) (Chiron Corporation); isoprinosine (inosine pranobex); Krestin (Sankyo); LC-9018 (Yakult); lentinan (Ajinomoto/Yamanouchi); LF-1695 (Fournier); methionine-enkephalin (TNI Pharmaceuticals; Sigma Chemicals); Minophagen C; muramyl tripeptide, MTP-PE (Ciba-Geigy); naltrexone ("Trexan" DuPont); Neutropin, RNA immunomodulator (Nippon Shingaku); Remune (Immune Response Corporation); Reticulose (Advanced Viral Research Corporation); shosaikoto and ginseng; thymic humoral factor; TP-05 (Thymopentin, Ortho Pharmaceuticals); Thymosin factor 5 and Thymosin 1; Thymostimulin; TNF (Tumor necrosis factor) manufactured by Genentech; and vitamin B preparations.

The preferred animal subject of the present invention is a mammal. By the term "mammal" is meant an individual belonging to the class Mammalia. The invention is particularly useful in the treatment of human patients.

The term "treating" means the administering to subjects a betulin or dihydrobetulin derivative for purposes which can include prevention, amelioration, or cure of a retroviral-related pathology.

Medicaments are considered to be provided "in combination" with one another if they are provided to the patient concurrently or if the time between the administration of each medicament is such as to permit an overlap of biological activity.

In one preferred embodiment, at least one betulin or dihydrobetulin derivative comprises a single pharmaceutical composition.

Pharmaceutical compositions for administration according to the present invention can comprise at least one betulin or dihydrobetulin derivative according to the present invention in a pharmaceutically acceptable form optionally combined with a pharmaceutically acceptable carrier. These compositions can be administered by any means that achieve their intended purposes. Amounts and regimens for the administration of a betulin derivative according to the present invention can be determined readily by those with ordinary skill in the clinical art of treating a retroviral pathology.

For example, administration can be by parenteral, such as subcutaneous, intravenous, intramuscular, intraperitoneal, transdermal, or buccal routes. Alternatively, or concurrently, administration can be by the oral route. The dosage administered depends upon the age, health and weight of the recipient, type of previous or concurrent treatment, if any, frequency of treatment, and the nature of the effect desired.

Compositions within the scope of this invention include all compositions comprising at least one betulin or dihydrobetulin derivative according to the present invention in an amount effective to achieve its intended purpose. While individual needs vary, determination of optimal ranges of effective amounts of each component is within the skill of the art. Typical dosages comprise about 0.1 to about 100 mg/kg body weight. The preferred dosages comprise about 1 to about 100 mg/kg body weight of the active ingredient. The most preferred dosages comprise about 10 to about 100 mg/kg body weight.

Therapeutic administration can also include prior, concurrent, subsequent or adjunctive administration of at least one additional betulin or dihydrobetulin derivative according to the present invention or other therapeutic agent, such as an anti-viral or immune stimulating agent. In such an approach, the dosage of the second drug can preferably be the same as or different from the dosage of the first therapeutic agent. Preferably, the drugs are administered on alternate days in the recommended amounts of each drug.

Administration of a compound of the present invention can also optionally include previous, concurrent, subsequent or adjunctive therapy using immune system boosters or immunomodulators. In addition to the pharmacologically active compounds, a pharmaceutical composition of the present invention can also contain suitable pharmaceutically acceptable carriers comprising excipients and auxiliaries which facilitate processing of the active compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 20 to 75 percent of active compound(s), together with the excipient.

Pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture, and processing the mixture of granules, after adding suitable auxiliaries, if desired or necessary, to obtain tablets or dragee cores.

Suitable excipients are, e.g., fillers such as saccharide, for example, lactose or sucrose, mannitol or sorbitol; cellulose preparations and/or calcium phosphates, such as tricalcium phosphate or calcium hydrogen phosphate; as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added such as the above-mentioned starches and also carboxymethyl starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions can be used, which can optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl cellulose phthalate are used. Dyestuffs or pigments can be added to the tablets or dragee coatings, for example, for identification or in order to characterize combinations of active compound doses.

Other pharmaceutical preparations which an be used orally include push-fit capsules made of gelatin, as well as soft, sealed capsules made of gelatin and a plasticizer such as glycerol or sorbitol. The push-fit capsules can contain the active compounds in the form of granules which can be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils or liquid paraffin. In addition, stabilizers can be added.

Possible pharmaceutical preparations which can be used rectally include, for example, suppositories which consist of a combination of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts. In addition, suspensions of the active compounds as appropriate oily injection suspensions can be administered. Suitable lipophilic solvents or vehicles include fatty oils, such as sesame oil, or synthetic fatty acid esters, such as ethyl oleate or triglycerides. Aqueous injection suspensions that can contain substances which increase the viscosity of the suspension include, for example, sodium carboxymethyl cellulose, sorbitol, and/or dextran. Optionally, the suspension can also contain stabilizers.

A pharmaceutical formulation for systemic administration according to the invention can be formulated for enteral, parenteral or topical administration. Indeed, all three types of formulation can be used simultaneously to achieve systemic administration of the active ingredient.

Suitable formulations for oral administration include hard or soft gelatin capsules, dragees, pills, tablets, including coated tablets, elixirs, suspensions, syrups or inhalations and controlled release forms thereof.

Solid dosage forms in addition to those formulated for oral administration include rectal suppositories.

The betulin or dihydrobetulin derivatives of the present invention can also be administered in the form of an implant when compounded with a biodegradable slow-release carrier. Alternatively, the betulin or dihydrobetulin derivatives of the present invention can be formulated as a transdermal patch for continuous release of the active ingredient.

Suitable formulations for topical administration include creams, gels, jellies, mucilages, pastes and ointments. Suitable injectable solutions include intravenous subcutaneous and intramuscular injectable solutions. Alternatively, the betulin or dihydrobetulin derivatives may be administered in the form of an infusion solution or as a nasal inhalation or spray.

The compounds of the present invention are synthesized by reacting betulin or dihydrobetulin with a suitable anhydride in anhydrous pyridine to esterify the betulin or dihydrobetulin. Betulin or dihyrobetulin was heated overnight at 95° C. with 6-fold of the appropriate anhydride in anhydrous pyridine in the presence of 4-(dimethylamino)pyridine. When TLC indicated complete consumption of starting material, the reaction solution was diluted with EtOAc and washed with 10% HCl solution. The EtOAc layer was then dried over $MgSO_4$ and subjected to column chromatography.

Scheme 1 depicts the synthesis route followed in Example 1, for compounds where $R_1$ and $R_2$ are $C_2$–$C_{20}$ substituted or unsubstituted carboxyacyl, and $R_3$ is hydrogen.

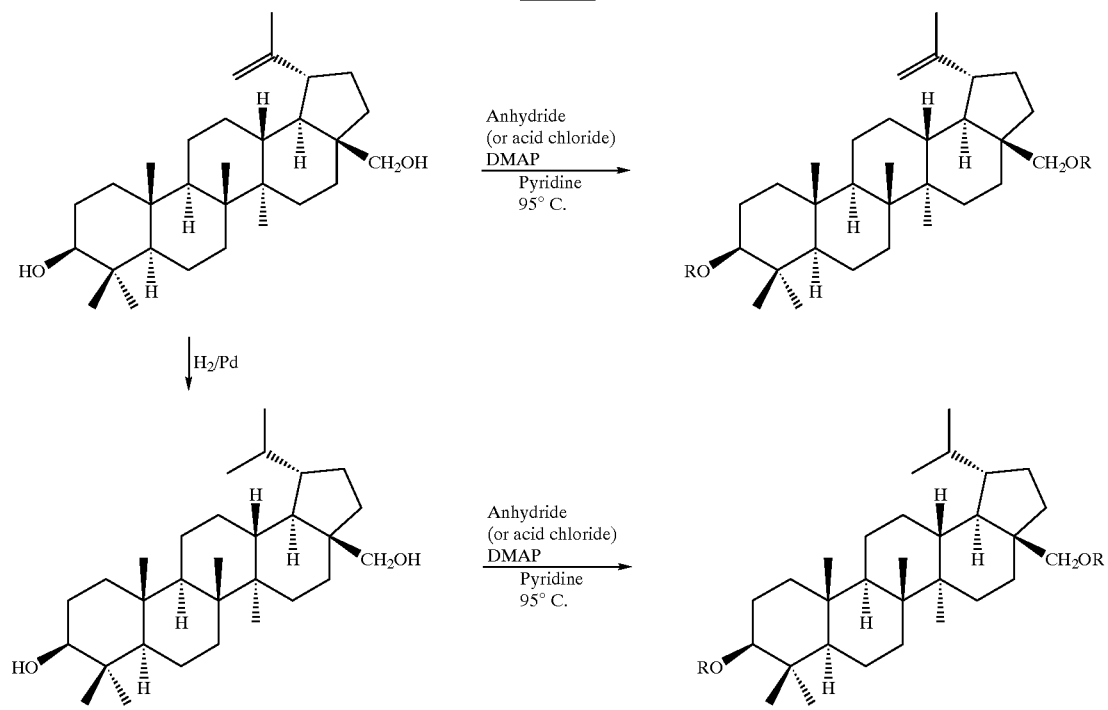

Scheme 1

Scheme 2 depicts the synthesis route followed in Example 1, for compounds where $R_1$ and $R_2$ are each $C_2$–$C_{20}$ substituted or unsubstituted carboxyacyl and $R_3$ is —$OR_4$, where $R_4$ is hydrogen or acyl, including $C_{2-20}$ substituted or unsubstituted carboxyacyl.

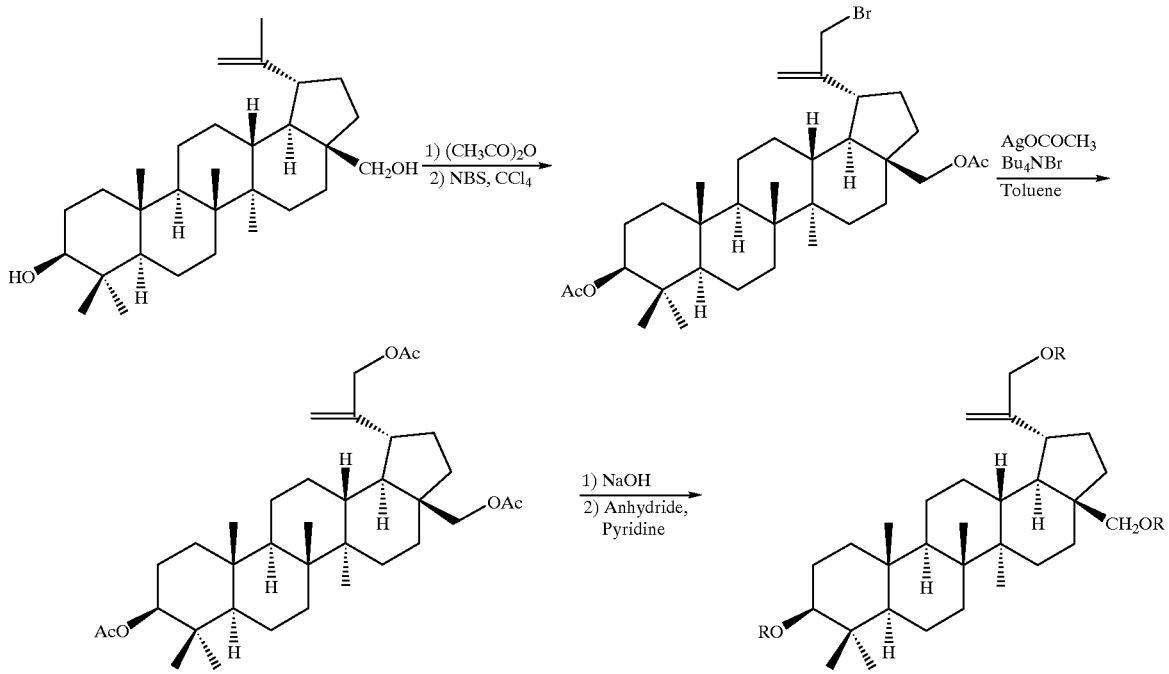

Scheme 2

Compounds 11 and 14 (structures appear following Example 1) were prepared by heating betulin and compound 13 overnight at 40° C. with 2-fold of 3,3-dimethylglutaryl anhydride in anhydrous pyridine in the presence of 4-(dimethylamino)pyridine, followed by a similar workup as for compounds 4–6 and 8–10. The residues were purified by column chromatography.

Compound 12 was synthesized by stirring compound 11 with 1.5 equivalent of pyridium chlorchromate in $CH_2Cl_2$ at room temperature. After 2 h, the black reaction mixture was diluted with $Et_2O$ and filtered through a short pack column. The filtrate was concentrated and chromatographed [n-hexane:acetone (4:1)] to yield compound 12 in a 72% yield.

A solution of betulin and triphenyl phosphine (4 equiv) in dry THF was added dropwise to diethyl azodicarboxylate (4 equiv) in an ice bath. The reaction solution was stirred for 12 h. After removing THF in vacuum, the residue was chromatographed with n-hexane:EtOAc (15:1) as eluent to afford compound 13.

The biological evaluation of HIV-1 inhibition was carried out according to established protocols, (Kashiwada, Y., et al., *J Med Chem.* 39:1016–1017 (1996); Hashimoto, F., et al., *Bioorg. & Med Chem.* 5:2133–2143 (1997)). The T cell line, H9, was maintained in continuous culture with complete medium (RPMI 1640 with 10% fetal calf serum supplemented with L-glutamine at 5% $CO_2$ and 37° C.). Aliquot of this cell line were only used in experiments when in log-phase growth. Test samples were first dissolved in dimethyl sulfoxide. The following final drug concentrations were routinely used for screening: 100, 20, 4 and 0.8 μg/ml. For active agents, additional dilutions were prepared for subsequent testing so that an accurate $EC_{50}$ value (defined below) could be achieved. As the test samples were being prepared, an aliquot of the H9 cell line was infected with HIV-1 (IIIB isolate) while another aliquot was mock-infected with complete medium. The stock virus used for these studies typically had a $TCID_{50}$ value of $10^4$ Infectious Units/ml. The appropriate amount of virus for a multiplicity of infection (moi) between 0.1 and 0.01 Infectious Units/cell was added to the first aliquot of H9 cells. The other aliquot only received culture medium, and these mock-infected cells were used for toxicity determinations ($IC_{50}$, defined below). After a 4 h incubation at 37° C. and 5% $CO_2$, both cell populations were washed three times with fresh medium and then added to the appropriate wells of a 24 well-plate containing the various concentrations of the test drug or culture medium (positive infected control/negative drug control). In addition, AZT was also assayed during each experiment as a positive drug control. The plates were incubated at 37° C. and 5% $CO_2$ for 4 days. Cell-free supernatants were collected on Day 4 for use in a p24 antigen ELISA assay. P24 antigen is a core protein of HIV and therefore is an indirect measure of virus present in the supernatants. Toxicity was determined by performing cell counts by a Coulter Counter on the mock-infected H9 cells which had either received culture medium (no toxicity), test sample, or AZT. If a test sample had suppressivecapability and was not toxic, its effects were reported in the following terms: $IC_{50}$, the concentration of test sample which was toxic to 50% of the mock-infected H9 cells; $EC_{50}$, the concentration of the test sample which was able to suppress HIV replication by 50%; and Therapeutic Index (TI), the ratio of $IC_{50}$ to $EC_{50}$.

The following examples are illustrative, but not limiting, of the method and compositions of the present invention. Other suitable modifications and adaptations of the variety of conditions and parameters normally encountered and obvious to those skilled in the art are within the spirit and scope of the invention.

EXAMPLE 1

Synthesis of Betulin and Dihydrobetulin Derivatives

Betulin or dihyrobetulin was heated overnight at 95° C. with 6-fold of the appropriate anhydride in anhydrous pyridine in the presence of 4-(dimethylamino)pyridine. When TLC indicated complete consumption of starting material, the reaction solution was diluted with EtOAc and washed with 10% HCl solution. The EtOAc layer was then dried over $MgSO_4$ and subjected to column chromatography.

Compounds 11 and 14 were prepared by heating betulin and compound 13 overnight at 40° C. with 2-fold of 3,3-dimethylglutaryl anhydride in anhydrous pyridine in the presence of 4-(dimethylamino)pyridine, followed by a similar workup as for compounds 4–6 and 8–10. The residues were purified by column chromatography.

Compound 12 was synthesized by stirring compound 11 with 1.5 equivalent of pyridium chlorchromate in $CH_2Cl_2$ at room temperature. After 2 h, the black reaction mixture was diluted with $Et_2O$ and filtered through a short pack column. The filtrate was concentrated and chromatographed [n-hexane:acetone (4:1)] to yield compound 12 in a 72% yield.

A solution of betulin and triphenyl phosphine (4 equiv) in dry THF was added dropwise to diethyl azodicarboxylate (4 equiv) in an ice bath. The reaction solution was stirred for 12 h. After removing THF in vacuum, the residue was chromatographed with n-hexane:EtOAc (15:1) as eluent to afford compound 13.

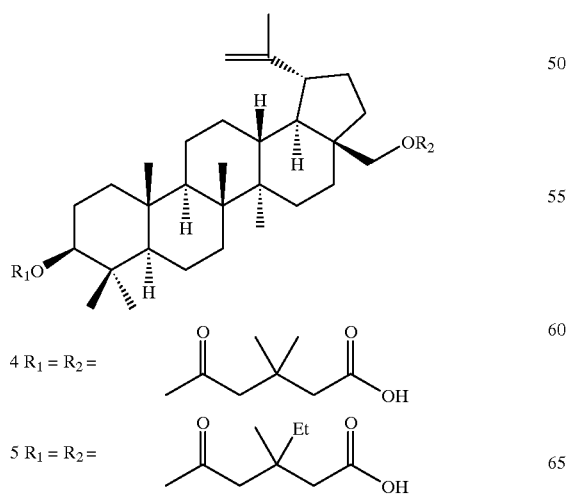

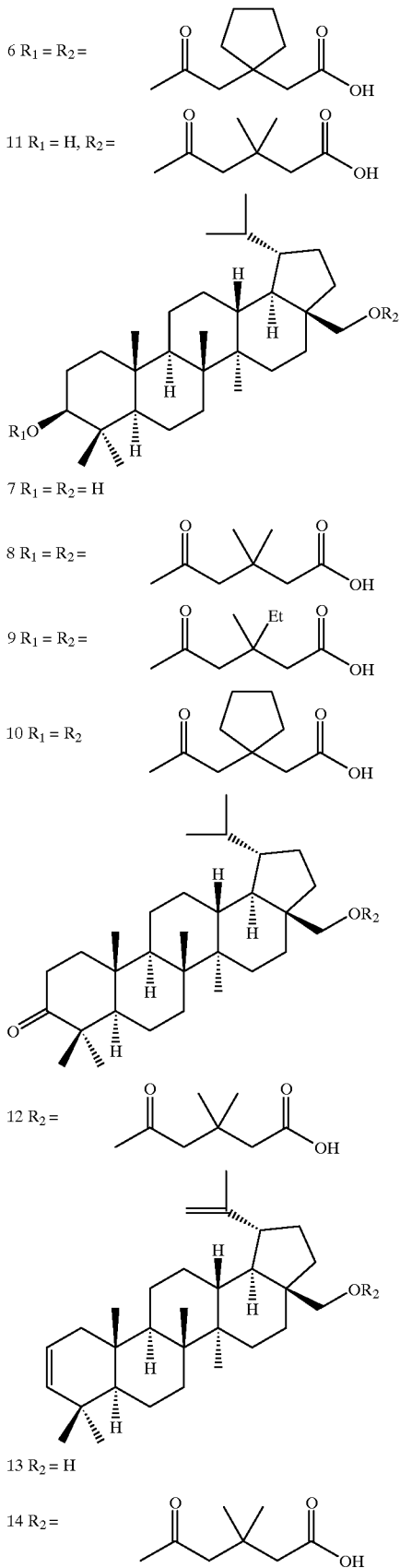

3,28-Di-O-(3',3'-dimethylglutaryl)-betulin (4)

yield 75% (after chromatography from CHCl$_3$-acetone [19:1]); an off-white amorphous powder; $[\alpha]^{25}_D$+21.9 (c=0.2, CHCl$_3$); $^1$H-NMR (CDCl$_3$): 0.84, 0.85, 0.86, 0.97, 1.03 (each 3H, s; 4-(CH$_3$)$_2$, 8-CH$_3$, 10-CH$_3$, 14-CH$_3$), 1.14 (12H, s; 3'-(CH$_3$)$_2$ and 3"-(CH$_3$)$_2$), 1.68 (3H, s; 20-CH$_3$), 2.42–2.50 (9H, m, H$_2$-2', 2", 4', 4"and H-19), 3.86, 4.30 (each 1H, d, J=11.1 Hz; H$_2$-28), 4.49 (1H, dd, J=5.2, 11.4 Hz; H-3), 4.59, 4.69 (each 1H, br s; H$_2$-29).

Anal. Calcd for C$_{44}$H$_{70}$O$_8$. 1/2 H$_2$O: C, 71.80; H, 9.72; found C, 71.73; H, 9.66.

3,28-Di-O-(3',3'-methylethylglutaryl)-betulin (5)

yield 94% (after chromatography from n-hexane:EtOAc [6:1]); an off-white amorphous powder; $[\alpha]^{25}_D$+13.2 (c=0.5, CHCl$_3$); $^1$H-NMR (CDCl$_3$): 0.85, 0.86, 0.91, 0.98, 1.04 (each 3H, s; 4-(CH$_3$)$_2$, 8-CH$_3$, 10-CH$_3$, 14-CH$_3$), 1.09 (6H, s; 3'-CH$_3$ and 3"-CH$_3$), 1.69 (3H, s; 20-CH$_3$), 2.41–2.57 (9H, m; H$_2$-2', 2", 4', 4"and H-19), 3.87, 4.30 (each 1H, d, J=11.0 Hz; H$_2$-28), 4.52 (1H, dd, J=4.6, 11.0 Hz; H-3), 4.60, 4.70 (each 1H, br s; H$_2$-29).

Anal. Calcd for C$_{46}$H$_{74}$O$_8$. 1/2 H$_2$O: C, 72.31; H, 9.89; found C, 72.34; H, 9.93.

3,28-Di-O-(3',3'-tetramethyleneglutaryl)-betulin (6)

yield 86% (after chromatography from n-hexane:EtOAc [8:1]); an off-white amorphous powder; $[\alpha]^{25}_D$+13.9 (c=0.99, CHCl$_3$); $^1$H-NMR (CDCl$_3$): 0.85, 0.86, (×2), 0.98, 1.04 (each 3H, s; 4-(CH$_3$)$_2$, 8-CH$_3$, 10-CH$_3$14-CH$_3$), 1.69 (3H, s; 20-CH$_3$), 2.45 (1H, dt; J=5.8, 10.6 Hz; H-19), 2.52–2.59 (8H, m, H$_2$-2', 2", 4', and 4"), 3.88, 4.29 (each 1H, d, J=11.1 Hz; H$_2$-28), 4.51 (1H, dd, J=5.0, 10.8 Hz; H-3), 4.60, 4.70 (each 1H, br s; H$_2$-29).

Anal. Calcd for C$_{48}$H$_{74}$O$_8$. H$_2$O: C, 72.33; H, 9.61; found C, 72.43; H, 9.51.

Dihydrobetulin (7)

yield 94%; a colorless powder; $^1$H-NMR (CDCl$_3$): 0.76, 0.77 (each 3H, d, J=3.4 Hz; 20-(CH$_3$)$_2$), 0.83, 0.85, 0.96, 0.97, 1.03 (each 3H, s; 4-(CH$_3$)$_2$, 8-CH$_3$, 10-CH$_3$, 14-CH$_3$), 3.20 (1H, dd, J=5.3, 11.0 Hz; H-3), 3.30, 3.79 (each 1H, d J=11.0 Hz; H$_2$-28). Anal. Calcd for C$_{30}$H$_{52}$O$_2$: C, 81.02; H, 11.78; found C, 81.05; H, 11.71.

3,28-Di-O-(3',3'-dimethyglutaryl)-dihydrobetulin (8)

yield 81% (after chromatography from CHCl$_3$-acetone [19:1]); an amorphous powder; $[\alpha]^{25}_D$−15.0 (c=0.2, CHCl$_3$); $^1$H-NMR (CDCl$_3$): 0.77, 0.84, (each 3H, d, J=6.7 Hz; 20-(CH$_3$)$_2$), 0.85, 0.86 (×2), 0.95, 1.04 (each 3H, s; 4-(CH$_3$)$_2$, 8-CH$_3$, 10-CH$_3$, 14-CH$_3$), 1.14 (12H, s; 3'-(CH$_3$)$_2$ and 3"-(CH$_3$)$_2$), 2.43–2.54 (8H, m, H$_2$-2', 2", 4', and 4"), 3.83, 4.29 (each 1H, d, J=11.0 Hz; H$_2$-28), 4.52 (1H, dd, J=4.8 11.0 Hz; H-3).

Anal. Calcd for C$_{44}$H$_{72}$O$_8$: C, 72.49; H, 9.95; found C, 72.28; H, 9.95.

3,28-Di-O-(3',3'-methylethylglutaryl)-dihydrobetulin (9)

yield 84% (after chromatography from n-hexane:EtOAc [6:1]); an off-white amorphous powder; $[\alpha]_D$−17.6 (c=0.49, CHCl$_3$); $^1$H-NMR (CDCl$_3$): 0.78, 0.85, (each 3H, d, J=6.6 Hz; 20-(CH$_3$)$_2$), 0.86×2, 0.87, 0.91, 1.05 (each 3H, s; 4-(CH$_3$)$_2$, 8-CH$_3$, 10-CH$_3$, 14-CH$_3$), 1.09 (6H, s; 3'-CH$_3$ and 3"-CH$_3$), 2.40–2.56 (8H, m, H$_2$-2', 2", 4', and 4"), 3.84, 4.30 (each 1H, d, J=11.0 Hz; H$_2$-28), 4.52 (1H, dd, J=4.6, 11.0 Hz; H-3), 4.60, 4.70 (each 1H, br s; H$_2$-29).

Anal. Calcd for C$_{46}$H$_{76}$O$_8$: C, 72.98; H, 10.12; found C, 73.08; H, 10.09.

3,28-Di-O-(3',3'-tetramethyleneglutaryl)-dihydrobetulin (10)

yield 89% (after chromatography from n-hexane:EtOAc [8:1]); an off-white amorphous powder; $[\alpha]^{25}_D$−18.2 (c=0.52, CHCl$_3$); $^1$H-NMR (CDCl$_3$): 0.78, 0.85, (each 3H, d, J=6.6 Hz; 20-(CH$_3$)$_2$), 0.85, 0.87 (×2), 0.96, 1.05 (each 3H, s; 4-(CH$_3$)$_2$, 8-CH$_3$, 10-CH$_3$, 14-CH$_3$), 2.52–2.63 (8H, m, H$_2$-2', 2", 4', and 4"), 3.84, 4.28 (each 1H, d, J=11.1 Hz; H$_2$-28), 4.51 (1H, dd, J=5.4, 10.3 Hz; H-3).

Anal. Calcd for C$_{48}$H$_{76}$O$_8$. 3/2H$_2$O: C, 71.34; H, 9.85; found C, 71.57; H, 9.53.

28-O-(3',3'-Dimethylglutaryl)-betulin (11)

yield 71% (after chromatography from n-hexane:acetone [9:1]); an off-white amorphous powder; $[\alpha]^{25}_D$+12.3 (c=0.49, CHCl$_3$); $^1$H-NMR (CDCl$_3$): 0.77, 0.83, 0.98×2, 1.04 (each 3H, s; 4-(CH$_3$)$_2$, 8-CH$_3$, 10-CH$_3$, 14-CH$_3$), 1.15 (6H, s; 3'-(CH$_3$)$_2$), 1.69 (3H, s, 20-CH$_3$), 2.40, 2.48 (1H, m, H-19), 2.48 (4H, s; H$_2$-2' and H$_2$-4), 3.20 (1H, dd,J=5.2, 10.9 Hz; H-3), 3.87, 4.29 (each 1H, d, J=11.1 Hz; H$_2$-28), 4.60, 4.70 (each 1H, br s; H$_2$-29).

Anal. Calcd for C$_{36}$H$_{60}$O$_5$. 1/4H$_2$O: C, 74.89; H, 10.59; found C, 74.89; H, 10.56.

3-Deoxy-3-oxo-28-O-(3',3'-dimethylglutaryl)-betulin (12)

yield 72% (after chromatography from n-hexane:acetone [4:1]); an off-white amorphous powder; $[\alpha]^{25}_D$+32.4 (c=0.33, CHCl$_3$); $^1$H-NMR (CDCl$_3$): 0.94, 1.00, 1.04, 1.08×2 (each 3H, s; 4-(CH$_3$)$_2$, 8-CH$_3$, 10-CH$_3$, 14-CH$_3$), 1.16 (6H, s; 3'-(CH$_3$)$_2$), 1.69 (3H, w; 20-CH$_3$), 2.41–2.54 (7H, m, H$_2$-2, 2', 4', and H-19), 3.87 4.30 (each 1H, d, J=11.1 Hz; H$_2$-28), 4.61, 4.70 (each 1H, br s; H$_2$-29).

Anal. Calcd for C$_{36}$H$_{58}$O$_5$: C, 76.24; H, 10.03; found C, 76.47; H, 10.31.

3-Deoxy-2,3-dihydro-betulin (13)

yield 74% (after chromatography from n-hexane:EtOAc [15:1]);[$\alpha$]$^{25}_D$+46.5 (c=0.2, CHCl$_3$); $^1$H-NMR (CDCl$_3$) 0.90, 0.93, 0.96, 0.99, 1.04 (each 3H, s; 4-(CH$_3$)$_2$, 8-CH$_3$, 10-CH$_3$, 14-CH$_3$), 1.68 (3H, s; 20-CH$_3$), 2.32–2.53 (2H, m, H-2a, and H-19), 2.85 (1H, ddd, J=5.5, 11.1, 11.1 Hz; H-2e), 4.61, 4.74 (each 1H, br, s; H$_2$-29), 9.65 (1H, s; H-28).

Anal. Calcd for C$_{30}$H$_{48}$O. 1/4H$_2$O: C, 83.95; H, 11.39; found C, 84.00; H, 11.34.

3-Deoxy-2,3-dihydro-28-O-(3',3'-dimethylglutaryl)-betulin (14)

yield 83% (after chromatography from n-hexane: CHCl$_3$ [8:2:1]); an off-white amorphous powder; $[\alpha]^{25}_D$+26.37

(c=0.49, CHCl$_3$); $^1$H-NMR (CDCl$_3$): 0.84, 0.85, 0.92, 0.97, 1.04 (each 3H, s; 4-(CH$_3$)$_2$, 8-CH$_3$, 10-CH$_3$, 14-CH$_3$), 1.13 (6H, s, 3'-CH$_3$)2), 1.67 (3H, s, 20-CH$_3$), 2.39–2.50 (1H, m, H-19), 2.45, 2.45 (each 2H, s; H$_2$-2'and H$_2$-4'), 3.86, 4.28 (each 1H, d, J=11.1 Hz; H$_2$-28), 4.58, 4.67 (each 1H, br, s; H$_2$-29), 5.34–5.37 (2H, m; H-2 and H-3).

Anal. Calcd for C$_{37}$H$_{60}$O$_4$: C, 78.12; H, 10.63; found C, 77.99; H, 10.47.

EXAMPLE 2

Pharmacological Activity

Compounds of the present invention were assayed for anti-HIV activity according to the following assay procedures. The T cell line, H9, and the promonocytic cell line, U937, were maintained separately in continuous culture with complete medium (RPMI 1640 with 10% fetal calf serum) at 5% CO$_2$ and 37° C. The cell lines were used in experiments only when in the logarithmic phase of growth, whereas uninfected peripheral blood mononuclear cells (PBMCs) were first stimulated with PHA (1 µg/mL) for three days. All cell targets were incubated with HIV-1 (IIIB isolate, TCID$_{50}$ 10$^4$IU/ml, at a multiplicity of infection of 0.01–0.01 IU/cell) for one hour at 37° C. and 5% CO$_2$. The cell lines and PBMCs were washed thoroughly to remove unadsorbed virions and resuspended at 4×10$^5$ cells/ml in complete medium or complete medium with 10% v/v interleukin 2 (IL-2), respectively. One ml. aliquots were placed into wells of 24-well culture plates containing an equal volume of test compounds (diluted in the appropriate culture medium). The toxicity of each compound was assessed by determining the number of compound-exposed uninfected cells that remained after four days at 37° C. and 5% CO$_2$. A p24 antigen ELISA assay was used to determine the level of virus released in the medium of the HIV-infected cultures. The p24 antigen assay used a HIV-1 anti-p24 specific monoclonal antibody as the capture antibody coated onto 96-well plates. Following a sample incubation period, rabbit serum containing antibodies for HIV-1 p24 was used to tag any p24 captured onto the microtiterwell surface. Peroxidase conjugated goat anti-rabbit serum was then used to tag HIV-1 p24 specific rabbit antibodies that had complexed with captured p24. The presence of p24 in test samples was then revealed by addition of substrate. The cutoff for the p24 ELISA assay was 12.5 pg/ml. P24 in the culture medium was quantitated against a standard curve containing known amounts of p24. The effective (EC$_{50}$) and inhibitory (IC$_{50}$) concentrations for anti-HIV activity and cytotoxicity, respectively, were determined.

TABLE 1

Anti-HIV Activities of Betulin and Related Derivatives

| Compound | Anti-HIV* Activity EC$_{50}$ (µM) | Cytotoxicity* IC$_{50}$ (µM) | Therapeutic* Index (TI = IC$_{50}$/EC$_{50}$) |
|---|---|---|---|
| 1 | 1.4 | 13.0 | 9.3 |
| 2 | 0.0023 | 4.5 | 1,974 |
| 3 | 23 | 43.7 | 1.9 |
| 4 | 0.00066 | 14.2 | 21,515 |
| 5 | 0.0053 | 18.4 | 3,476 |
| 6 | 0.077 | 20.5 | 267 |
| 7 | NT | NT | NT |
| 8 | 0.0047 | 10.6 | 2,253 |
| 9 | 0.075 | 18.7 | 248 |
| 10 | 0.58 | 21.6 | 37 |
| 11 | 3.6 | 28.2 | 7.8 |
| 12 | 10.0 | 29.2 | 2.9 |
| 13 | 11.9 | 31.9 | 2.7 |
| 14 | 5.4 | 28.3 | 5.2 |
| AZT | 0.015 | 500 | 33,333 |

NT: not tested
*all the data represented as an average of at least two experiments.

Compounds 3–6, 8–14 and AZT were examined for anti-HIV activity in H-9 lymphocytes as shown in Table 1. Betulin (3) with a C-28 hydroxy group was less potent than betulinic acid (1) with a C-28 carboxylic acid. However, adding two 3', 3'-dimethyglutaryl esters to betulin (3) gave compound 4, which showed significantly enhanced activity and a remarkably high therapeutic index (TI) with EC$_{50}$ and TI values of 0.00066 µM and 21,515, respectively. Because compound 4 was about 3-fold more potent and had a higher TI than compound 2, the C-28 acyl side chain led to improved activity. When the 3' substitution was changed to 3'-ethyl-3'-methyl (5) or 3',3'-tetramethylene (6), the EC$_{50}$ values were still in the nanomolar range, but the compounds were less active compared with compound 4. Saturation of the C20–C29 double bond in compound 4 gave compound 8 and led to about a 7- and 9-fold drop in activity and in TI, respectively. Similarly, the dihydro compounds 9 and 10 showed less inhibition than the unsaturated 5 and 6. Because compounds 6 and 10, which contain a 3',3'-tetramethylene glutaryl group exhibited the least activity and lowest TI values among the two series of compounds (4–6 and 8–10, respectively), additional bulk at the 3' position is not favored for anti-HIV activity.

Compound 11 is esterified only at the C-28 position and is 6-fold more potent compared to 3. However, 11 is much less potent than 4, confirming the importance of the 3-acyl side chain for increased activity. Replacing the 3-hydroxy group of 11 with a ketone decreased activity further (compare 11 and 12). Dehydration of betulin's "A" ring gave the unsaturated 13, which had a slightly improved EC$_{50}$ compared with 3. The acylated product, compound 14 displayed increased anti-HIV activity, but perhaps due to the lack of a 3-acyl moiety, the EC$_{50}$ of 14 was only 5.4 µM.

In conclusion, the diacylated betulin derivative 4 showed remarkable anti-HIV activity even greater than that of the betulinic acid derivative 2. The C-28 acyl side chain could further increase anti-HIV activity as well as TI, but a C-3 acyl side chain was essential for optimal activity. The 3',3'-dimethyl glutaryl group gave the best activity among three different 3',3'-disubstituted esters. In addition, betulin derivatives (4–6) were more potent than their corresponding dihydrobetulin compounds (8–10).

Having now fully described this invention, it will be understood to those of ordinary skill in the art that the same

What is claimed is:

1. A compound of Formula I:

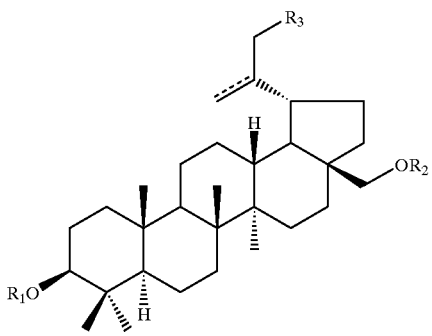

I or a pharmaceutically acceptable salt thereof; wherein $R_1$ is a $C_2$–$C_{20}$ substituted or unsubstituted carboxyacyl, $R_2$ is a $C_2$–$C_{20}$ substituted or unsubstituted carboxyacyl; and $R_3$ is hydrogen, halogen, amino, optionally substituted mono- or di-alkylamino, or —$OR_4$, where $R_4$ is hydrogen, $C_{1-4}$ alkanoyl, benzoyl, or $C_2$–$C_{20}$ substituted or unsubstituted carboxyacyl;

wherein the dashed line represents an optional double bond between C20 and C29; with the proviso that when $R_3$ is hydrogen, $R_1$ and $R_2$ are not both selected from the group consisting of succinyl, maleyl fumaroyl and glutaryl.

2. A compound according to claim 1, wherein $R_1$ and $R_2$ are each $C_2$–$C_{20}$ substituted or unsubstituted carboxyacyl, and $R_3$ is hydrogen.

3. A compound according to claim 1, wherein $R_1$ and $R_2$ are each $C_2$–$C_{20}$ substituted or unsubstituted carboxyacyl, and $R_3$ is halogen or —$OR_4$, where $R_4$ is hydrogen or substituted or unsubstituted carboxyacyl.

4. A compound according to claim 1, wherein $R_3$ is one of:

i. hydrogen;

ii. —O—C(O)CH$_2$CR'R"(CH$_2$)$_b$COOH, where R' and R" are each $C_{1-4}$ alkyl, or R' is hydrogen and R" is $C_{1-4}$ alkyl, or R' and R" are taken together to form a di-, tri, tetra- or pentamethylene linkage, and b is from zero to twelve;

iii. —O—C(O)CH$_2$O(CH$_2$)$_a$COOH, where a is from zero to 12; or iv. —OH.

5. A compound according to claim 1, wherein $R_3$ is:

where R' and R" are each methyl, and b is zero or one.

6. A compound according to claim 1, wherein:
$R_1$ and $R_2$ are each one of:

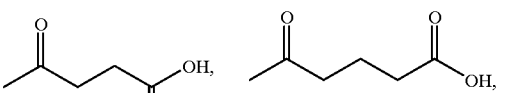

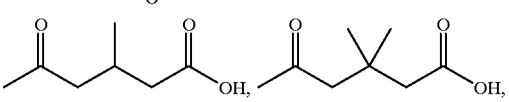

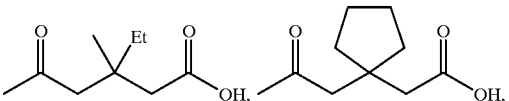

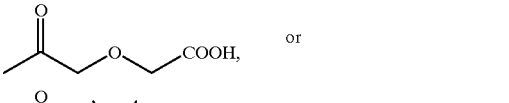

$R_3$ is hydrogen, hydroxy, or one of:

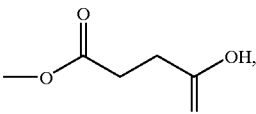

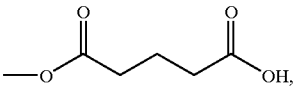

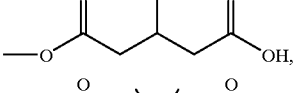

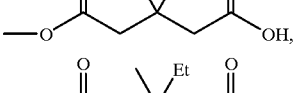

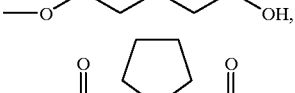

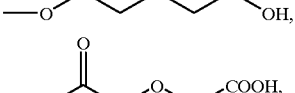

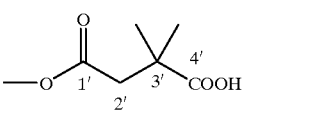

7. A pharmaceutical composition comprising one or more compounds according to claim 1, or a pharmaceutically acceptable ester, salt, ether, sulfate, or glucuronide thereof, and a pharmaceutically acceptable carrier.

8. A pharmaceutical composition according to claim 7, further comprising a drug selected from an anti-viral agent or an immunostimulating agent.

9. A pharmaceutical composition according to claim 8, wherein said antiviral agent is selected from the group consisting of nevirapine, delavirdine, efavirenz, saquinavir, ritonavir, indinavir, nelfinavir, amprenavir, hydroxyurea, interleukin-2, gamma globulin, amantadine, guanidine hydroxybenzimidazole, interferon-α, interferon-β, interferon-γ, a thiosemicarbazone, methisazone, rifampin, ribavirin, a pyrimidine analog, a purine analog, foscarnet, phosphonoacetic acid, acyclovir, a dideoxynucleoside, and gancyclovir.

10. A pharmaceutical composition according to claim 8, wherein said antiviral agent is a nucleoside analog.

11. A pharmaceutical composition according to claim 10, wherein said nucleoside analog is selected from the group consisting of AZT, 3TC, ddI, ddC, D4T, abacavir, and adefovir.

12. A compound of Formula I:

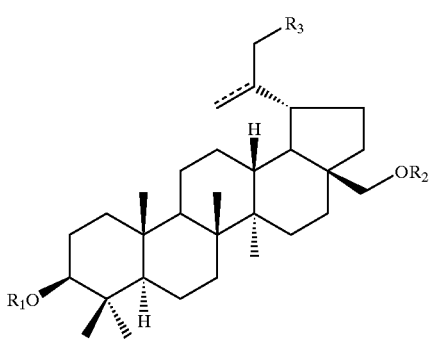

I or a pharmaceutically acceptable salt thereof; wherein
$R_1$ and $R_2$ are independently selected from the group consisting of:
(a) —C(O)CH$_2$CR'R"(CH$_2$)$_b$COOH, wherein R' and R" are each $C_{1-4}$ alky, or R' is hydrogen and R" is $C_{1-4}$ alkyl, or R' and R" are taken together to form a di-, tri, tetra- or pentamethylene linkage, and b is from zero to twelve, and
(b) —C(O)CH$_2$O(CH$_2$)$_a$COOH, wherein a is from zero to twelve; and
$R_3$ is hydrogen, halogen, amino, optionally substituted mono- or di-alkylamino, or —OR$_4$, wherein $R_4$ is hydrogen, $C_{1-4}$ alkanoyl, benzoyl, or $C_2$–$C_{20}$ substituted or unsubstituted carboxyacyl;
wherein the dashed line represents an optional double bond between $C_{20}$ and C29.

13. The compound of claim 12, wherein $R_1$ and $R_2$ are each, independently:

—C(O)CH$_2$CR'R"(CH$_2$)$_b$COOH, wherein R' and R" are each $C_{1-4}$ alkyl, or R' is hydrogen and R" is $C_{1-4}$ alkyl, or R' and R" are taken together to form a di-, tri, tetra- or pentamethylene linkage, and b is from zero to twelve.

14. The compound of claim 13, wherein b is zero to 4.

15. The compound of claim 14, selected from the group consisting of:
3,28-di-O-(3',3'-methylethylglutaryl)-betulin;
3,28-di-O-(3',3'-tetramethyleneglutaryl)-betulin;
3,28-di-O-(3',3'-methylethylglutaryl)-dihydrobetulin; and
3,28-di-O-(3',3'-tetramethyleneglutaryl)-dihydrobetulin.

16. The compound of claim 14, wherein R' and R" are each methyl, and b is zero or 1.

17. The compound of claim 16, wherein:
$R_1$ and $R_2$ are each

$R_3$ is hydrogen.

18. The compound of claim 17, selected from the group consisting of:
3,28-di-O-(3',3'-dimethylglutaryl)-betulin; and
3,28-di-O-(3',3 '-dimethylglutaryl)-dihydrobetulin.

19. The compound of claim 12, wherein $R_1$ and $R_2$ are each, independently:

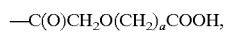

—C(O)CH$_2$O(CH$_2$)$_a$COOH, wherein a is from zero to twelve.

20. The compound of claim 12, wherein $R_3$ is one of:
i. hydrogen;
ii. —O—C(O)CH$_2$CR'R"(CH$_2$)$_b$COOH, where R' and R" are each $C_{1-4}$ alkyl, or R' is hydrogen and R" is $C_{1-4}$ alkyl, or R' and R" are taken together to form a di-, tri, tetra- or pentamethylene linkage, and b is from zero to twelve;
iii. —O—C(O)CH$_2$O(CH$_2$)$_a$COOH, where a is from zero to 12; or
iv. —OH.

21. The compound of claim 12, wherein $R_3$ is:

—O—C(O)CH$_2$CR'R"(CH$_2$)$_b$COOH, where R' and R" are each methyl, and b is zero or one.

22. The compound of claim 12, wherein $R_3$ is hydrogen, hydroxy,

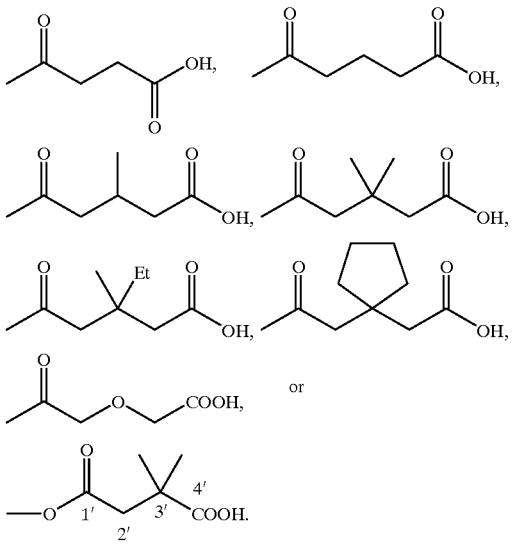

23. A pharmaceutical composition comprising one or more compounds according to claim 12, or a pharmaceutically acceptable ester, salt, ether, sulfate, or glucuronide thereof, and a pharmaceutically acceptable carrier.

24. A pharmaceutical composition according to claim 23, further comprising a drug selected from an anti-viral agent or an immunostimulating agent.

25. A pharmaceutical composition according to claim 24, wherein said antiviral agent is selected from the group consisting of nevirapine, delavirdine, efavirenz, saquinavir, ritonavir, indinavir, nelfinavir, amprenavir, hydroxyurea, interleukin-2, gamma globulin, amantadine, guanidine hydroxybenzimidazole, interferon-α, interferon-β, interferon-γ, a thiosemicarbazone, methisazone, rifampin, ribavirin, a pyrimidine analog, a purine analog, foscarnet, phosphonoacetic acid, acyclovir, a dideoxynucleoside, and gancyclovir.

26. A pharmaceutical composition according to claim 23, wherein said antiviral agent is a nucleoside analog.

27. A pharmaceutical composition according to claim 26, wherein said nucleoside analog is selected from the group consisting of AZT, 3TC, ddI, ddC, D4T, abacavir, and adefovir.

28. A method for inhibiting a retroviral infection in cells or tissue of an animal comprising administering an effective retroviral inhibiting amount of a pharmaceutical composition comprising a pharmaceutically acceptable carrier and a compound of Formula I:

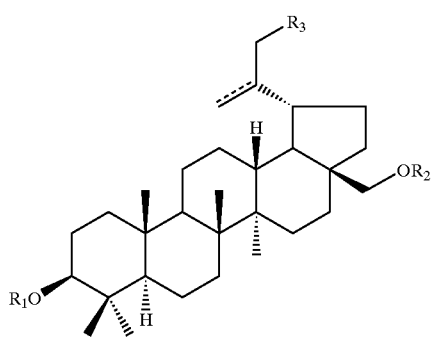

or a pharmaceutically acceptable ester, salt, ether, sulfate, or glucuronide thereof; wherein $R_1$ is a $C_2$–$C_{20}$ substituted or unsubstituted carboxyacyl, $R_2$ is a $C_2$–$C_{20}$ substituted or unsubstituted carboxyacyl; and $R_3$ is hydrogen, halogen, amino, optionally substituted mono- or di-alkylamino, or —$OR_4$, where $R_4$ is hydrogen, $C_{1-4}$ alkanoyl, benzoyl, or $C_2$–$C_{20}$ substituted or unsubstituted carboxyacyl;

wherein the dashed line represents an optional double bond between C20 and C29.

29. The method of claim 28, wherein said composition is administered to provide said compound in an amount ranging from about 0.1 to about 100 mg/kg body weight.

30. The method of claim 29, wherein said composition is administered to provide said compound in an amount ranging from about 1 to about 10 mg/kg body weight.

31. The method of claim 30, wherein said animal is a human.

32. A method for treating a patient suffering from a retroviral related pathology, comprising administering to said subject a retroviral inhibiting effective amount of a pharmaceutical composition comprising a pharmaceutically acceptable carrier and a compound of Formula I:

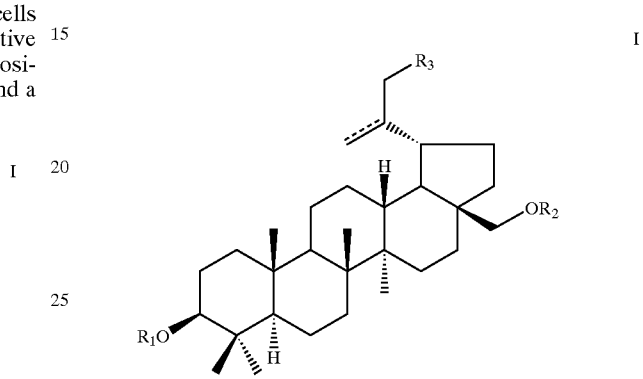

or a pharmaceutically acceptable ester, salt, ether, sulfate, or glucuronide thereof; wherein $R_1$ is a $C_2$–$C_{20}$ substituted or unsubstituted carboxyacyl, $R_2$ is a $C_2$–$C_{20}$ substituted or unsubstituted carboxyacyl; and $R_3$ is hydrogen, halogen, amino, optionally substituted mono- or di-alkylamino, or —$OR_4$, where $R_4$ is hydrogen, $C_{1-4}$ alkanoyl, benzoyl, or $C_2$–$C_{20}$ substituted or unsubstituted carboxyacyl;

wherein the dashed line represents an optional double bond between C20 and C29.

33. The method of claim 32, wherein said retroviral related pathology is an HIV infection.

* * * * *

UNITED STATES PATENT AND TRADEMARK OFFICE
CERTIFICATE OF CORRECTION

PATENT NO. : 6,172,110 B1
DATED : January 9, 2001
INVENTOR(S) : Kuo-Hsiung Lee et al.

It is certified that error appears in the above-identified patent and that said Letters Patent is hereby corrected as shown below:

Column 16,
Line 32, "10 $R_1 = R_2$" should read -- 10 $R_1 = R_2 =$ --.
Lines 35-45, the structure, should read

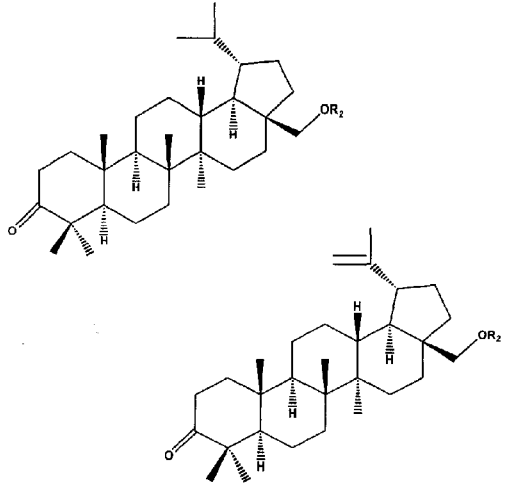

Column 21,
Line 40, a comma should be inserted after "maleyl".

Column 23,
Line 47, "$C_{20}$" should read -- C20 --.

UNITED STATES PATENT AND TRADEMARK OFFICE
CERTIFICATE OF CORRECTION

PATENT NO.   : 6,172,110 B1
DATED        : January 9, 2001
INVENTOR(S)  : Kuo-Hsiung Lee et al.

It is certified that error appears in the above-identified patent and that said Letters Patent is hereby corrected as shown below:

Column 24,
Lines 36-58, after "The compound of claim 12, wherein $R_3$ is hydrogen, hydroxy," the remainder of the claim should read:

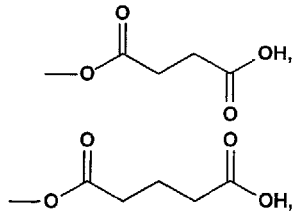

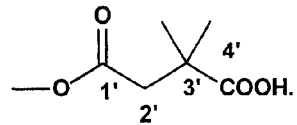

Column 25,
Line 8, "claim 23" should read -- claim 24 --.

Signed and Sealed this

Twenty-second Day of April, 2003

JAMES E. ROGAN
*Director of the United States Patent and Trademark Office*